United States Patent
Maier et al.

(10) Patent No.: US 6,673,745 B2
(45) Date of Patent: *Jan. 6, 2004

(54) HERBICIDAL 3,5-DIFLUOROPYRIDINES

(75) Inventors: Thomas Maier, Mainz (DE); Stefan Scheiblich, Mainz (DE); Helmut S. Baltruschat, Schweppenhausen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/759,564

(22) Filed: Jan. 12, 2001

(65) Prior Publication Data

US 2001/0011064 A1 Aug. 2, 2001

Related U.S. Application Data

(62) Division of application No. 09/078,005, filed on May 13, 1998, now Pat. No. 6,310,006.
(60) Provisional application No. 60/048,169, filed on May 30, 1997.

(51) Int. Cl.$^7$ .................. A01N 43/34; C07D 401/12
(52) U.S. Cl. .............. 504/25 D; 504/251; 504/256; 546/256; 546/261; 546/280.4; 546/303
(58) Field of Search .............. 504/251, 250, 504/256; 546/261, 256, 303, 280.4

(56) References Cited

U.S. PATENT DOCUMENTS

| | | | |
|---|---|---|---|
| 5,747,423 A | 5/1998 | Scheiblich et al. | 504/251 |
| 5,750,470 A | 5/1998 | Morimoto et al. | 504/253 |
| 5,824,624 A | 10/1998 | Kleemann et al. | 504/242 |
| 5,849,758 A | 12/1998 | Kleemann et al. | 514/269 |
| 5,922,726 A | 7/1999 | Scheiblich et al. | 514/269 |
| 5,972,842 A | 10/1999 | Maier et al. | 504/253 |
| 6,110,871 A | * 8/2000 | Maier et al. | 504/250 |

FOREIGN PATENT DOCUMENTS

| | | |
|---|---|---|
| EP | 0 723 960 | 7/1996 |
| EP | 0 820 996 A1 | 1/1998 |
| RU | 2035447 | 1/1998 |
| WO | WO 96/06096 | 2/1996 |
| WO | WO 98/04550 | 2/1998 |

OTHER PUBLICATIONS

Oldham, P.H. et al., "Homolytic Reactions of Perfluoroaromatic Compounds", J. Chem. Soc. B (1970), (7), 1346–9 Coden: JCSPAC, XP002078755.

Anderson, L.P. et al., "Synthesis of 2–substituted tetrafluoropyridines", Chem. Commun. (1968), (22). 1433 Coden: CCOMA8 XP002078756.

Chemical Abstracts 119:162355 (1993) N. Toshkhodzhaev et al., "Synthesis and Some Properties of Dyes Based on 6–substituted 2, 3,5–Trichloropyridines".

Toshkhodzhaev, N.A., et al., "Synthesis And Some Properties of 6–Substituted–2,3,5–Trichloropyridine–Based Dyes," Vyssh. Uchebn. Zaved. 36 (1993) 97–101.

* cited by examiner

Primary Examiner—Jane Fan
(74) Attorney, Agent, or Firm—Keil & Weinkauf

(57) ABSTRACT

The invention relates to novel compounds of formula I:

(I)

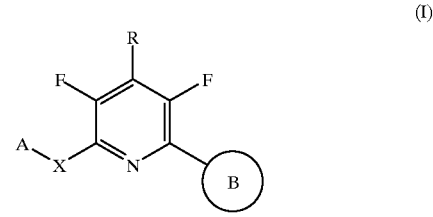

wherein R, A, B and X have the meaning given in claim 1; and the agronomically acceptable salts or N-oxides thereof, and to herbicidal compositions containing such compounds as active ingredients.

13 Claims, No Drawings

HERBICIDAL 3,5-DIFLUOROPYRIDINES

This is a divisional application of Ser. No. 09/078,005 filed on May 13, 1998, now U.S. Pat. No. 6,310,006 issued on Oct. 30, 2001, which claims the benefit of Ser. No. 60/048,169, filed May 30, 1997.

BACKGROUND OF THE INVENTION

This invention relates to certain novel trisubstituted 3,5-difluoropyridines, to the preparation of such compounds, to herbicidal compositions containing such compounds, and to a method of combating undesired plant growth using such compounds.

Pyridines and their derivatives have many uses in the pharmaceutical area as well as in agriculture (herbicides, fungicides, acaricides, anthelmintics, bird repellents), as reagents, intermediates and chemicals for the polymer and textile industry.

The broad generic formula of the International patent application WO 96/06096 embraces fluorinated 2-azolyl-5-aryloxypyridines.

Similar 2-aryl-5-aryloxypyridines are disclosed by EP 0 723 960. The co-pending U.S. patent application Ser. No. 08/680,193 (Case 33,272) discloses 2-thienyl-5-aryloxypyridines. However, there is no hint to 3,5-difluoropyridines in any of these documents.

The co-pending U.S. patent application Ser. No. 08/688,591 (Case 33,273) discloses 2,6-bisaryloxy-3,5-difluoropyridines.

Although many of the known compounds show considerable activity against various weeds, they are not completely satisfying with regard to their selectivity or because of their persistence.

The compounds according to the present invention combine high herbicidal activity with the necessary selectivity and enhanced soil degradation.

SUMMARY OF THE INVENTION

We have now found that, surprisingly, 2-aryloxy-6-aryl-3,5-difluoropyridines show excellent herbicidal activity at low dosages combined with higher selectivity in crops than those disclosed in the aforementioned patent applications.

Accordingly, the present invention provides novel compounds of the general formula I

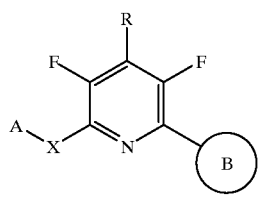

(I)

wherein

A represents an optionally substituted aryl group or an optionally substituted 5- or 6-membered nitrogen-containing heteroaromatic group or a difluorobenzodioxolyl group;

B represents an optionally substituted phenyl or thienyl group;

R represents a halogen atom or an optionally substituted alkyl, alkenyl, alkinyl, alkoxy, alkoxyalkyl, alkylthio, alkylamino, dialkylamino, alkylsulphinyl, alkylsulphonyl group or a nitro, cyano, hydroxy, amino, haloalkyl, haloalkoxy, haloalkylthio or $SF_5$ group, and, X represents an oxygen or a sulfur atom;

and the agronomically acceptable salts or N-oxides thereof.

The new compounds show an excellent selective herbicidal activity in certain crops, such as maize and rice, and enhanced soil degradation.

It is another object of the invention to provide methods for controlling undesired plant growth by contacting said plants with a herbicidally effective amount of the new compounds.

It is another object of the invention to provide selective herbicidal compositions containing the new compounds as active ingredients.

It is another object of the invention to provide new processes for the preparation of the new compounds.

Those and other objects and features of the invention will become more apparent from the detailed description set forth hereinbelow.

DETAILED DESCRIPTION OF THE PREFERRED EMBODIMENTS

It has surprisingly been found that the novel compounds of formula I in which R, A, B and X have the meaning given above for formula I, and the agronomically acceptable salts or N-oxides thereof, show an excellent herbicidal activity against a broad range of weeds.

An aryl group as substituent or part of other substituents or in the definition of A is suitably an optionally substituted phenyl group. Within the definition of A the 5- or 6-membered heteroaryl group comprises optionally substituted 5- or 6-membered heterocycles containing one or more nitrogen and/or oxygen and/or sulfur atoms, 1 to 3 nitrogen atoms being preferred. Examples of such groups are pyrazolyl, imidazolyl, triazolyl, tetrazolyl, pyridyl, pyrazinyl, pyrimidyl, pyridazinyl, isoxazolyl, isothiazolyl and triazinyl groups. As far as A is concerned the definition "aryl" does also include bicyclic systems which consist of a benzene ring fused with a 5- or 6-membered heterocyclic ring as defined above and in turn the 5- or 6-membered heterocycles may be fused with a benzene ring. Another preferred embodiment of A is a difluorobenzodioxolyl group of formula

A preferably represents a phenyl, pyridyl or pyrazolyl group being substituted by one or more of the same or different substituents selected from halogen atoms, alkyl groups, alkoxy groups, cyano groups, haloalkyl groups, haloalkoxy groups, alkylthio groups, haloalkylthio groups and $SF_5$ groups, in particular wherein A has a substituent in the meta-position relative to the point of attachment. Most preferred wherein A is meta-substituted by a fluorine or chlorine atom, or a trifluoromethyl, trifluoromethoxy or difluoromethoxy group.

B preferably represents a phenyl or thienyl group being substituted by one or more of the same or different substituents selected from halogen atoms, alkyl groups, alkoxy groups, cyano groups, haloalkyl groups, haloalkoxy groups, alkylthio groups, haloalkylthio groups, alkylsulfonyl and $SF_5$ groups, in particular wherein if B is a phenyl group it has a substituent in the para-position relative to the point of attachment. Most preferred wherein B is a phenyl group being para-substituted by a fluorine or chlorine atom, or a trifluoromethyl, trifluoromethoxy or difluoromethoxy group.

R represents preferably a halogen atom or an optionally substituted alkyl, alkenyl, alkoxy, alkoxyalkyl, alkylthio group or a nitro or cyano group.

X is preferably an oxygen atom.

Generally, if any of the above mentioned moieties comprises an alkyl, alkenyl or alkynyl group, such groups, unless otherwise specified, may be linear or branched and may contain 1 to 6, preferably 1 to 4, carbon atoms. Examples of such groups are methyl, ethyl, propyl, vinyl, allyl, propargyl, isopropyl, butyl, isobutyl and tertiary-butyl groups. The alkyl portion of a haloalkyl, haloalkoxy, haloalkylthio, alkylthio or alkoxy group suitably has from 1 to 4 carbon atoms, preferably 1 or 2 carbon atoms. The number of carbon atoms in the alkoxyalkyl, alkoxyalkoxy or dialkoxyalkyl groups is up to 6, preferably up to 4, e.g. methoxymethyl, methoxymethoxy, methoxyethyl, ethoxymethyl, ethoxyethoxy, dimethoxymethyl.

"Halogen" means a fluorine, chlorine, bromine or iodine atom, preferably fluorine, chlorine or bromine. Haloalkyl moieties of any groups within the definitions used herein and as such can contain one or more halogen atoms. Haloalkyl, haloalkoxy and haloalkylthio are preferably mono-, di-, tri- or perfluoroalkyl, -alkoxy and -alkylthio, especially trifluoromethyl, pentafluoroethyl, trifluoromethoxy, difluoromethoxy, difluoromethylthio, trifluoromethylthio or 2,2,2-trifluoroethoxy groups.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds.

There may be one or more of the same or different substituents present in each part of the molecules. In relation to moieties defined above as comprising an optionally substituted alkyl group, including alkyl parts of haloalkyl, alkoxy, alkylthio, haloalkoxy, alkylamino and dialkylamino groups, specific examples of such substituents include phenyl, halogen atoms, nitro, cyano, hydroxyl, $C_{1-4}$-alkoxy, $C_{1-4}$-haloalkoxy and $C_{1-4}$-alkoxycarbonyl groups.

In relation to moieties defined above as comprising an optionally substituted aryl or heteroaryl group, optional substituents include halogen, especially fluorine, chlorine and bromine atoms, and nitro, cyano, amino, hydroxy, phenoxy, $C_{1-4}$-alkyl, $C_{1-4}$-alkoxy, $C_{1-4}$-haloalkyl, $C_{1-4}$-haloalkenyl, $C_{1-4}$-haloalkoxy, $C_{1-4}$-haloalkylthio, $C_{1-4}$-alkylsulfonyl and halosulfanyl groups such as $SF_5$. In the case of phenyl-groups 1 to 5 substituents may suitably be employed, in the case of thienyl-groups 1 to 3 substituents may suitably be employed, 1 or 2 substituents being preferred.

Typically haloalkyl, haloalkoxy and haloalkylthio groups are trifluoromethyl, pentafluoroethyl, trifluoromethoxy, difluoromethoxy, 2,2,2-trifluoroethoxy and trifluoromethylthio groups.

In formula I A preferably represents a group of formula a, b or c:

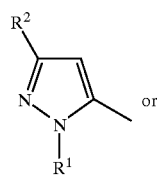

(a)

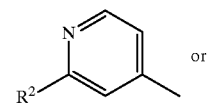

(b)

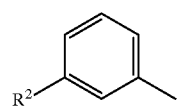

(c)

wherein $R^1$ is $C_{1-3}$ alkyl and $R^2$ is $C_{1-3}$ alkyl, $C_{1-3}$ haloalkyl, a halogen atom, cyano, $C_{1-3}$ haloalkoxy or $C_{1-3}$ haloalkylthio; while B preferably represents a group of formula d or e:

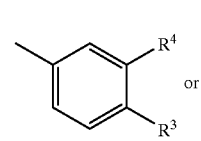

(d)

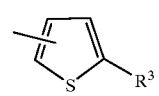

(e)

wherein $R^3$ is $C_{1-4}$ alkyl $C_{1-3}$ haloalkyl, a halogen atom, cyano, $C_{1-3}$ haloalkoxy or $C_{1-3}$ haloalkylthio and $R^4$ is hydrogen, halogen or $C_{1-3}$ alkyl Preferred are those compounds of formula I, wherein the thienyl group (e) is attached to the 3,5-difluoropyridine moiety in the 2-position relative to the sulfur atom.

R preferably represents a $C_{1-4}$ alkyl, in particular methyl, a $C_{1-4}$ alkoxy, in particular methoxy, or a cyano group.

Particularly preferred are the compounds of formula IA and IB:

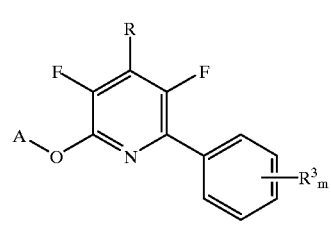

(IA)

wherein A represents 3-trifluoromethylphenyl, 2-chloropyrid-4-yl, 2-trifluoromethylpyrid-4-yl, 2-difluoromethoxypyrid-4-yl or 1-methyl-3-trifluoromethylpyrazol-5-yl, R has the meaning given above; $R^3$ each independently represent a hydrogen atom or a fluorine atom, one or two of them also a chlorine or bromine or a trifluoromethyl, trifluormethoxy or a cyano group, one of them can further be a $C_1$–$C_4$-alkyl group, particularly tert-butyl, and m is 0 or an integer selected from 1 to 5, preferably 1 or 2;

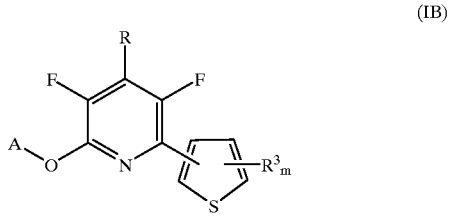
(IB)

wherein A represents 3-trifluoromethylphenyl, 2-chloropyrid-4-yl, 2-trifluoromethylpyrid-4-yl, 2-difluoromethoxypyrid-4-yl or 1-methyl-3-trifluoromethylpyrazol-5-yl, R having the meaning given above; $R^3$ each independently represent a hydrogen atom or a fluorine atom, one or two of them also a chlorine or bromine atom, or a trifluoromethyl, trifluormethoxy or a cyano group, one of them can further be a $C_1$–$C_4$-alkyl group, particularly tert-butyl, and m is 0 or an integer selected from 1 to 3, preferably 1.

The thienyl group may be attached in the 2- or 3-position with respect to the sulfur atom. 2-thienyl groups are preferred.

Suitably, R represents a halogen atom or an optionally substituted alkyl, alkoxy group or a cyano group.

Preferably, R represents an optionally substituted $C_{1-6}$ alkyl group or $C_{1-6}$ alkoxy group which is unsubstituted, or substituted by one or more moieties independently selected from halogen atoms. In particular R denotes a fluorine or chlorine atom or a methyl, ethyl or methoxy group.

The invention is exemplified by the following specific compounds:

3,5-difluoro-4-methyl-2-(1'-methyl-3'-trifluoromethylpyrazol-5'-yloxy)-6-(4"-trifluoromethylphenyl)pyridine, 3,5-difluoro-4-methyl-2-(3'-trifluoromethylphenoxy)-6-(4"-trifluoromethyl-phenyl)pyridine, 3,5-difluoro-4-ethyl-2-(3'-trifluoromethylphenoxy)-6-(4"-trifluoromethyl-phenyl)pyridine, 3,5-difluoro-4-ethyl-2-(1'-methyl-3'-trifluoromethylpyrazol-5'-yloxy)-6-(4"-trifluoromethylphenyl)pyridine, 6-(4'-chlorophenyl)-3,5-difluoro-4-methyl-2-(1"-methyl-3"-trifluoromethylpyrazol-5"-yloxy)pyridine, 6-(4'-chlorophenyl)-3,5-difluoro-4-methyl-2-(3"-trifluoromethylphenoxy)pyridine, 2-(2'-chloropyrid-4'-yloxy)-3,5-difluoro-4-methyl-6-(4"-trifluoromethylphenyl)pyridine, 3,5-difluoro-4-methyl-2-(2'-trifluoromethylpyrid-4'-yloxy)-6-(4"-trifluoromethylphenyl)pyridine, 3,5-difluoro-2-(2"-difluoromethoxypyrid-4'-yloxy)-4-methyl-6-(4"-trifluoromethylphenyl)pyridine, 6-(5"-chlorothien-2"-yl)-3,5-difluoro-4-methyl-2-(1'-methyl-3'-trifluoromethylpyrazol-5'-yloxy)-pyridine, 2-(2'-chloropyrid-4'-yloxy)-3,5-difluoro-4-methyl-6-(3"-trifluoromethylphenyl)pyridine, 3,5-difluoro-4-methyl-2-(1'-methyl-3'-trifluoromethylpyrazol-5'-yloxy)-6-(5"-trifluoromethylthien-2"-yl)pyridine, 3,5-difluoro-4-methyl-2-(1'-methyl-3'-trifluoromethylpyrazol-5'-yloxy)-6-(4"-fluorophenyl)pyridine, 3,5-difluoro-4-methoxy-2-(1'-methyl-3'-trifluoromethylpyrazol-5'-yloxy)-6-(4"-trifluoromethylphenyl)pyridine, 3,5-difluoro-4-ethoxy-2-(1-methyl-3'-trifluoromethylpyrazol-5'-yloxy)-6-(4"-trifluoromethylphenyl)pyridine, 3,5-difluoro-4-methoxy-2-(3'-trifluoromethylphenoxy)-6-(4"-trifluoromethylphenyl) pyridine, 3,5-difluoro-4-methyl-2-(2'-cyanopyrid-4'-yloxy)-6-(4"-trifluoromethylphenyl)pyridine, 3,5-difluoro-4-methyl-2-(1'-methyl-3'-cyanopyrazol-5'-yloxy)-6-(4"-trifluoromethylphenyl)pyridine, 3,5-difluoro-2-(3'-difluoromethoxyphenoxy)-4-methyl-6-(4"-trifluoromethylphenyl)pyridine, 3,5-difluoro-4-methyl-2-(3'-trifluoromethoxyphenoxy)-6-(4"-trifluoromethylphenyl) pyridine, 2-(3'-cyanophenoxy)-3,5-difluoro-4-methyl-6-(4"-trifluoromethylphenyl)pyridine, 3,5-difluoro-4-methyl-2-(1'-methyl-3'-isopropylpyrazol-5'-yloxy)-6-(4"-trifluoromethylphenyl)pyridine, 3,5-difluoro-4-methyl-2-(1'-methyl-3'-difluoromethoxypyrazol-5'-yloxy)-6-(4"-trifluoromethylphenyl)pyridine, 3,5-difluoro-4-methyl-2-(2'-(2",2",2"-trifluoroethoxy)pyrid-4'-yloxy)-6-(4'"-trifluoromethylphenyl)pyridine, 3,5-difluoro-4-methyl-6-(4'-trifluoromethylphenyl)-2-(3"-trifluoromethylthio-phenoxy)pyridine, 3,5-difluoro-4-methyl-2-(4'-tert-butyl-phenyl)-2-(3'"-trifluoromethylphenoxy)pyridine, 3,5-difluoro-4-methyl-2-(1'-ethyl-3'-trifluoromethylpyrazol-5'-yloxy)-6-(4"-trifluoromethylphenyl)pyridine, 3,5-difluoro-4-methyl-6-(4'-isopropylphenyl)-2-(3"-trifluoromethylphenoxy)pyridine, 6-(4'-bromophenyl)-3,5-difluoro-4-methyl-2-(3"-trifluoromethylphenoxy)pyridine, 3,5-difluoro-4-methyl-2-(1'-methyl-3'-trifluoromethyl-4'-fluoropyrazol-5'-yloxy)-6-(4"-trifluoromethylphenyl)pyridine, 3,5-difluoro-4-methyl-2-(1'-methyl-3'-trifluoromethyl-4'-chloropyrazol-5'-yloxy)-6-(trifluoromethylphenyl)pyridine, 3,5-difluoro-4-methyl-2-(1'-methyl-3'-trifluoromethylpyrazol-5'-yloxy)-6-(4"-trifluoromethoxyphenyl)pyridine, 3,5-difluoro-4-methyl-2-(1'-methyl-3'-trifluoromethylpyrazol-5'-yloxy)-6-(4"-trifluoromethylthiophenyl)pyridine, 3,5-difluoro-6-(4'-difluoromethylthiophenyl)-4-methyl-2-(1"-methyl-3"-trifluoromethylpyrazol-5"-yloxy)pyridine, 3,5-difluoro-4-methyl-6-(4'-ethylphenyl)-2-(1"-methyl-3"-trifluoromethylpyrazol-5"yloxy)pyridine, 3,5-difluoro-6-(3',4'-difluorophenyl)-4-methyl-2-(1"-methyl-3"-trifluoromethylpyrazol-5"-yloxy)pyridine, 3,5-difluoro-6-(2',4'-difluorophenyl)-4-methyl-2-(1"-methyl-3"-trifluoromethylpyrazol-5"-yloxy)pyridine, 3,5-difluoro-4-chloro-2-(1'-methyl-3'-trifluoromethylpyrazol-5'-yloxy)-6-(4"-trifluoromethylphenyl)pyridine, 3,5-difluoro-4-chloro-2-(3'-trifluoromethylphenoxy)-6-(4"-trifluoromethyl-phenyl)pyridine, 3,5-difluoro-4-methylthio-2-(1'-methyl-3'-trifluoromethylpyraxol-5'-yloxy)-6-(4"-trifluoromethylphenyl)pyridine, and 3,5-difluoro-4-methylthio-2-(3'-trifluoromethylphenoxy)-6-(4"-trifluoromethyl-phenyl)pyridine, 4-cyano-3,5-difluoro-2-(1'-methyl-3'-trifluoromethylpyrazol-5'-yloxy)-6-(4"-trifluoromethylphenyl)pyridine, 4-cyano-3,5-difluoro-2-(3'-trifluoromethylphenoxy)-6-(4"-trifluoromethyl-phenyl) pyridine, 6-(4'-chlorophenyl)-4-cyano-3,5-difluoro-2-(1"-methyl-3"-trifluoromethylpyrazol-5"-yloxy)pyridine, 6-(4'-chlorophenyl)-4-cyano-3,5-difluoro-2-(3"-trifluoromethylphenoxy)pyridine, 2-(2'-chloropyrid-4'-yloxy)4-cyano-3,5-difluoro-6-(4"-trifluoromethylphenyl) pyridine, 4-cyano-3,5-difluoro-2-(2'-trifluoromethylpyrid-4'-yloxy)-6-(4"-trifluoromethylphenyl)pyridine, 6-(5"-chlorothien-2"-yl)-4-cyano-3,5-difluoro-2-(1'-methyl-3'-trifluoromethyl-pyrazol-5'-yloxy)-pyridine.

The compounds are oils, gums, or, predominantly, crystalline solid materials. They are superior through their valuable herbicidal properties. For example, they can be used in agriculture or related fields for the control of undesired plants. The compounds of general formula I according to the invention possess a high herbicidal activity within a wide concentration range and at low dosages, and may be used in agriculture without any difficulties, in particular for the selective control of undesired plants such as *Alopecurus myosuroides, Echinochloa crus-galli, Setaria viridis, Galium aparine, Stellaria media, Veronica persica, Lamium purpureum, Viola arvensis, Abutilon theophrasti, Ipomoea purpurea* and *Amaranthus retroflexus* by pre- and post-emergence application, particularly in certain crops, such as maize and rice.

The compounds according to the invention can be prepared by conventional methods, particularly as follows:

(A) A suitable process for the preparation of the compounds of general formula I comprises the reaction of a compound of formula II:

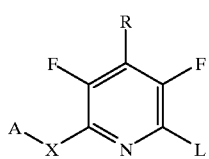

(II)

in which A, R, X and n have the meaning given and L is a leaving group, with a compound of general formula III,

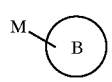

(III)

in which B and m have the meaning given, and M represents a free or complexed metal selected from the group consisting of Li, Mg, Zn, B, Sn, in particular Li, MgHal, or B(OH)$_2$, preferably under the conditions of a cross coupling reaction. Suitable leaving groups L are e.g. alkyl- and arylsulfonyl, alkyl- and arylsulfonyloxy, nitro, halogen, particularly fluorine, chlorine and bromine groups.

The cross coupling reaction may be carried out as a rule in the presence of a transition metal complex, as for example described in Tetrahedron 48 (1992) 8117, and Chem. Scr. 26 (1986) 305. Preferred transition metals are Pd or Ni. Compounds of general formula III may be prepared and isolated separately or may be prepared in situ.

(B) Alternatively a compound of formula IV:

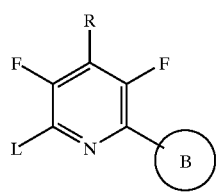

(IV)

with a compound of general formula V

 (V)

wherein

A, B, R, and X are defined as above;

L represents a suitable leaving group; and

M$^1$ represents a metal atom.

The reactions according to (A) and (B) may be carried out in the absence or presence of a solvent which promotes the reaction or at least does not interfere with it. Preferred are polar, aprotic or protic solvents, suitably being N,N-dimethylformamide, dimethylsulfoxide, sulfolane, acetonitrile, methyl ethyl ketone, or an ether, such as tetrahydrofurane or dioxane, or alcoholes, or water, or mixtures thereof. The reaction is carried out at a temperature between ambient temperature and the reflux temperature of the reaction mixture, preferably at elevated temperature, especially at reflux temperature.

The reactions may be carried out in the presence of a basic compound such as an alkali hydroxide, bicarbonate or carbonate, e.g. sodium or potassium hydroxide, bicarbonate or carbonate, an alkali alkoxide, e.g. sodium ethoxide, or an organic base such as triethylamine.

A hydroxy compound used in the above reactions may be present in form of a salt, preferably as a salt of an alkali metal, particularly of sodium or potassium. The presence of a copper salt may be suitable.

Suitable leaving groups L are e.g. alkyl- and arylsulfonyl, alkyl- and arylsulfonyloxy, perfluoroalkylsulfonyloxy, nitro and halogen, particularly fluorine, chlorine and bromine groups.

For compounds of formula II or IV, certain substituents R like alkyl, alkoxy, alkylthio, alkylamino, dialkylamino, amino or halo, can be introduced onto the pyridine ring by displacement of a alkyl- or arylsulfonyl, alkyl- or arylsulfonyloxy, nitro, or halogen group, or of a aryl- or hetaryloxy group like A—O group, wherein A has the meaning given. Halogen atoms may also be introduced by diazotization of a amino group.

The compounds used as starting material are partly known and partly novel. The invention relates to the novel intermediates, in particular to the compounds of formula IV, which can be prepared analogously to known methods.

Intermediates of formula II and IV can suitably be prepared from compounds of formula VI,

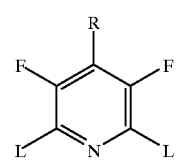

(VI)

in which R and L have the meaning given above, by conventional methods known in pyridine chemistry, as described in: G. R. Newkome, "Pyridine and its Derivatives", in The Chemistry of Heterocyclic Compounds, Vol.14, Part 5, Eds. A. Weissberger and E. C. Taylor, John Wiley & Sons, New York—Chichester—Brisbane—Toronto—Singapore 1984.

For the preparation of the intermediates of formula II the compound of formula VI is reacted with a compound of formula V essentially under the same conditions given for method (B).

For the preparation of the intermediates of formula IV the compound of formula VI is reacted with a compound of formula III essentially under the same conditions given for method (A).

The compounds of formula VI, wherein both leaving groups L are fluoro atoms, but R is different from a fluoro atom, are obtainable from commercially available pentafluoropyridine.

The compounds of formulae II, IV and VI may be synthesized from pentafluoropyridine, wherein the fluorine atoms at the 2-, 4- and 6-position can be replaced, e.g.

a) by groups of formula AX, which in turn can be replaced stepwise by a suitable group R, or b) by groups of formula R at position 4 followed by replacement of the fluorine atom at position 2 with AX or B.

The following acids are suitable for the preparation of the agronomically acceptable salts of the compounds of formula I: hydrohalides like hydrochloric or hydrobromic acid, phosphoric acid, nitric acid, sulfuric acid, mono- or bifunctional carboxylic acids and hydroxycarboxylic acids like acetic acid, maleic acid, succinic acid, fumaric acid, citric acid, salicylic acid, sorbic acid or lactic acid and sulfonic acids like p-toluenesulfonic acid or naphthalene-1,5-diyl-disulfonic acid. The agronomically acceptable salts of the compounds of formula I are prepared according to conventional salt formation procedures, for example by dilution of a compound of formula I in a suitable organic solvent, addition of an acid and isolation of the salt formed by, for example, filtration and optional purification by washing with an inert solvent.

The present invention also provides the use of the compounds of formula I as herbicides. Further, in accordance with the invention there is provided a method of combating undesired plant growth at a locus by treating the locus with a composition according to the invention or an effective amount of a compound of formula 1. As a useful action is by foliar spray application, the locus is most suitably the plants in a crop area, typical crops being cereals, maize, soy bean, sunflower or cotton. However, application may also be to the soil for those compounds having pre-emergence herbicidal action, or to the water of paddy rice fields. The dosage of active ingredient used may, for example be in the range of from 0.005 to 3 kg/ha, preferably 0.01 to 1 kg/ha.

The compounds of general formula I have been found to have herbicidal activity. Accordingly, the invention further provides a herbicidal composition which comprises an active ingredient, which is at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

| | Emulsion Concentrate (EC) | |
|---|---|---|
| Active Ingredient | Compound of Example 2 | 30% (w/v) |
| Emulsifier(s) | Atlox ® 4856 B/Atlox ® 4858 B [1] (mixture containing calcium alkyl aryl sulfonate, fatty alcohol ethoxylates and light aromatics/mixture containing calcium alkyl aryl sulfonate, fatty alcohol ethoxylates and light aromatics) | 5% (w/v) |
| Solvent | Shellsol ® A [2] (mixture of $C_9$–$C_{10}$ aromatic hydrocarbons) | to 1000 ml |
| | Suspension Concentrate (SC) | |
| Active Ingredient | Compound of Example 1 | 50% (w/v) |
| Dispersing agent | Soprophor ® FL [3] (polyoxyethylene polyaryl phenyl ether phosphate amine salt) | 3% (w/v) |
| Antifoaming agent | Rhodorsil ® 422 [3] (nonionic aqueous emulsion of polydimethylsiloxanes) | 0.2% (w/v) |
| Structure agent | Kelzan ® S [4] (Xanthan gum) | 0.2% (w/v) |
| Antifreezing agent | Propylene glycol | 5% (w/v) |
| Biocidal agent | Proxel ® [5] (aqueous dipropylene glycol solution containing 20% 1,2-benisothiazolin-3-one) | 0.1% (w/v) |
| Water | | to 1000 ml |
| | Wettable Powder (WP) | |
| Active Ingredient | Compound of Example 1 | 60% (w/w) |
| Wetting agent | Atlox ® 4995 [1] (polyoxyethylene alkyl ether) | 2% (w/w) |
| Dispersing agent | Witcosperse ® D-60 [6] (mixture of sodium salts of condensed naphthalene sulfonic acid and alkylarylpolyoxy acetates) | 3% (w/w) |
| Carrier/Filler | Kaolin | 35% (w/w) |
| | Water Dispersible Granules (WG) | |
| Active Ingredient | Compound of Example 2 | 50% (w/w) |
| Dispersing/Binding agent | Witcosperse ® D-450 [6] (mixture of sodium salts of condensed naphthalene sulfonic acid and alkyl sulfonates) | 8% (w/w) |
| Wetting agent | Morwet ® EFW [6] (formaldehyde condensation product) | 2% (w/w) |
| Antifoaming agent | Rhodorsil ® EP 6703 [3] (encapsulated silicone) | 1% (w/w) |
| Disintegrant | Agrimer ® ATF [7] (cross-linked homopolymer of N-vinyl-2-pyrrolidone) | 2% (w/w) |
| Carrier/Filler | Kaolin | 35% (w/w) |

[1] available from ICI Surfactants
[2] available from Deutsche Shell AG
[3] available from Rhône-Poulenc
[4] available from Kelco Co.
[5] available from Zeneca
[6] available from Witco
[7] available from International Speciality Products The compositions of this invention can also comprise other compounds having biological activity, e.g. compounds having similar or complementary pesticidal activity or compounds having plant growth regulating, fungicidal/ herbicidal or insecticidal activity. These mixtures of pesticides can have a broader spectrum of activity than the compound of general formula I alone. Furthermore, the other pesticide can have a synergistic effect on the pesticidal activity of the compound of general formula I.

The active ingredients according to the invention can be employed alone or as formulations in combination with conventional herbicides. Such combinations of at least two herbicides can be included in the formulation or also added in a suitable form with the preparation of the tank mix. For such mixtures at least one of the following known herbicides can be used:

2,4-D, 2,4-DB, 2,4-DP, acetochlor, acifluorfen, alachlor, alloxydim, ametrydione, amidosulfuron, asulam, atrazin, azimsulfuron, benfuresate, bensulfuron, bentazon, bifenox, bromobutide, bromoxynil, butachlor, cafenstrole, carfentrazone, chloridazon, chlorimuron, chlorpropham, chlorsulfuron, chlortoluron, cinmethylin, cinosulfuron, clomazone, clopyralid, cyanazin, cycloate, cyclosulfamuron, cycloxydim, daimuron, desmedipham, di-methazone, dicamba, dichlobenil, diclofop, diflufenican, dimethenamid, dithiopyr, diuron, eptame, esprocarb, ethiozin, fenoxaprop, flamprop-M-isopropyl, flamprop-M-methyl, fluazifop, fluometuron, fluoroglycofen, fluridone, fluroxypyr, flurtamone, fluthiamid, fomesafen, glufosinate, glyphosate, halosafen, haloxyfop, hexazinone, imazamethabenz, imazamethapyr, imazamox, imazapyr, imazaquin, imazethapyr, ioxynil, isoproturon, isoxaben, isoxaflutole, lactofen, MCPA, MCPP, mefenacet, metabenzthiazuron, metamitron, metazachlor, methyidimron, metolachlor, metribuzin, metsulfuron, molinate, nicosulfuron, norflurazon, oryzalin, oxadiargyl, oxasulfuron, oxyfluorfen, pendimethalin, picloram, picolinafen, pretilachlor, propachlor, propanil, prosulfocarb, pyrazosulfuron, pyridate, qinmerac, quinchlorac, quizalofopethyl, sethoxydim, simetryne, sulcotrione, sulfentrazone, sulfosate, terbutryne, terbutylazin, thiameturon, thifensulfuron, thiobencarb, tralkoxydim, triallate, triasulfuron, tribenuron, triclopyr, trifluralin.

Mixtures with other active ingredients like fungicides, insecticides, acaricides and nematicides are possible.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

The structures of the compounds prepared in the following examples were additionally confirmed by NMR and mass spectrometry.

EXAMPLE 1

3,5-Difluoro4-methyl-2-(1-methyl-3-trifluoromethylpyrazol-5-yloxy)-6-(4-trifluoromethylphenyl)pyridine 1A 4-methyl-2,3,5-trifluoro-6-(4-trifluoromethylphenyl) pyridine Butyl lithium (2.7 ml, 6.7 mmol, 2.5 M solution in hexane) is added to a solution of 1-bromo-4-trifluoromethyl benzene (1.0 ml, 7.3 mmol) in anhydrous diethyl ether (10 ml) at −20 ° C. The mixture is stirred for 60 min at −20 ° C. and for 60 min at 10° C. After cooling to −40° C. 4-methyl-2,3,5,6-tetrafluoropyridine (1.1 g, 6.6 mmol) is added. The resulting mixture is stirred for 120 min at −30 ° C. and then is allowed to warm to ambient temperature. After 2 days at ambient temperature the mixture is washed twice with saturated aqueous ammonium chloride. The layers are separated and the organic layer is dried with anhydrous magnesium sulfate and filtered. After removal of the solvents in vacuo, the crude product is purified by flash column chromatography (silica gel, pentane/ethyl acetate=9/1 by volume) yielding colorless crystals of 4-methyl-2,3,5-trifluoro-6-(4-trifluoromet (0.5 g,1.7 mmol) of mp. 52° C.

1 B 3,5-difluoro-4-methyl-2-(1'-methyl-3'-trifluoromethylpyrazol-5'-yloxy)-6-(4"-trifluoromethylphenyl)pyridine A mixture of 5-hydroxy-1-methyl-3-trifluoromethylpyrazole (0.31 g, 1.9 mmol), potassium carbonate (0.3 g, 2.1 mmol) and 4-methyl-2,3,5-trifluoro-6-(4-trifluoromethylphenyl)pyridine 1A (0.5 g, 1.7 mmol) in anhydrous sulfolane (2 ml) is heated to 120 ° C. for 24 hours. After cooling to ambient temperature the mixture is diluted with ethyl acetate/pentane (1/1 by volume) and filtered through a bed of silica gel. The filtrate is washed 10 times with water. After drying and evaporation of the organic layer, the residue is purified by column chromatography (silica gel: pentane/ethyl acetate 8/2 by volume). One obtains 0.14 g (0.32 mmol) of a colorless oil.

EXAMPLE 2

3,5-Difluoro-4-methyl-6-4-trifluoromethylphenyl)-2-(3-trifluoromethylphenoxy)pyridine 2A 4-methyl-2,3,5-trifluoro-6-(3-trifluoromethylphenoxy) pyridine To a solution of 3-trifluoromethyl phenol (13.2 ml, 0.11 mol) in anhydrous DMF (200 ml) is added sodium hydride (4.8 g, 60 %, 0.12 mol). After 30 min at ambient temperature the solution is added to another solution of 4-methyl-2,3,5, 6-tetrafluoropyridine (16.5 g, 0.1 mol) in anhydrous acetonitrile (700 ml) at 50° C. during 3 hours. The resulting mixture is then stirred for 1 hour at 50° C. and 16 hours at 75° C. The solvents are removed in vacuo and to the residue is added ethyl acetate/pentane (1000 ml, 1/1 by volume). The mixture is washed twice with 2M NaOH and 5 times with water. After drying and evaporation of the organic layer, the residue is purified by vacuum destillation. One obtains a colorless oil (23.3 g, 76 mmol, 76 % yield, bp. 76 ° C. at 0.025 mbar) of 4-methyl-2,3,5-trifluoro-6-(3-trifluoromethylphenoxy)pyridine.

2B 3,5-Difluoro4-methyl-6-(4-trifluoromethylphenyl)-2-(3-trifluoromethylphenoxy)pyridine Butyl lithium (2.6 ml, 6.6 mmol, 2.5 M solution in hexane) is added to a solution of 1-bromo-4-trifluoromethyl benzene (0.84 ml, 6 mmol) in anhydrous diethyl ether (5 ml) at −30° C. The mixture is stirred for 60 min at −20 ° C. and for 60 min at 10° C. The solution is allowed to warm to ambient temperature. This solution is then added to a mixture of 4-methyl-2,3,5-trifluoro-6-(3-trifluoromethylphenoxy)pyridine 2A (1.5 g, 5 mmol) in anhydrous diethyl ether (100 ml) at −50° C. during 2.5 hours. The mixture is further stirred for 7 hours at −50° C. and washed with saturated aqueous ammonium chloride and water. After drying and evaporation of the organic layer, the residue is purified by vacuum destillation. One obtains colorless crystals (0.37 g, 0.85 mmol, bp. 130 ° C. at 0.01–0.02 mbar) of mp. 87° C.

EXAMPLES 3–41

Further Examples are prepared according to the general method of Example 1 and are listed in Table 1.

TABLE 1

[Structure: pyridine ring with F at 3,5 positions, R at 4-position, A-O at 6-position, and phenyl at 2-position bearing $R^3$ and $R^4$ substituents]

| Ex. No. | A | R | $R^3$ | $R^4$ |
|---|---|---|---|---|
| 3 | 3-($CF_3$)-phenyl | $C_2H_5$ | $CF_3$ | H |
| 4 | 1-($CH_3$)-3-($CF_3$)-pyrazol-5-yl | $C_2H_5$ | $CF_3$ | H |
| 5 | 1-($CH_3$)-3-($CF_3$)-pyrazol-5-yl | $CH_3$ | Cl | H |
| 6 | 4-($CF_3$)-phenyl | $CH_3$ | Cl | H |
| 7 | 2-Cl-pyrid-4-yl | $CH_3$ | $CF_3$ | H |
| 8 | 2-($CF_3$)-pyrid-4-yl | $CH_3$ | $CF_3$ | H |
| 9 | 2-($CF_2O$)-pyrid-4-yl | $CH_3$ | $CF_3$ | H |
| 10 | 2-Cl-pyrid-4-yl | $CH_3$ | H | 3-$CF_3$ |
| 11 | 1-($CH_3$)-3-($CF_3$)-pyrazol-5-yl | $CH_3$ | F | H |
| 12 | 1-($CH_3$)-3-($CF_3$)-pyrazol-5-yl | $CH_3O$ | $CF_3$ | H |
| 13 | 1-($CH_3$)-3-($CF_3$)-pyrazol-5-yl | $C_2H_5O$ | $CF_3$ | H |
| 14 | 3-($CF_3$)-phenyl | $CH_3O$ | $CF_3$ | H |
| 15 | 2-(CN)-pyrid-4-yl | $CH_3$ | $CF_3$ | H |
| 16 | 1-($CH_3$)-3-(CN)-pyrazol-5-yl | $CH_3$ | $CF_3$ | H |
| 17 | 3-($CHF_2O$)-phenyl | $CH_3$ | $CF_3$ | H |
| 18 | 3-($CF_3O$)-phenyl | $CH_3$ | $CF_3$ | H |
| 19 | 3-(CN)-phenyl | $CH_3$ | $CF_3$ | H |
| 20 | 1-($CH_3$)-3-(i-$C_3H_7$)-pyrazol-5-yl | $CH_3$ | $CF_3$ | H |
| 21 | 1-($CH_3$)-3-($CF_2O$)-pyrazol-5-yl | $CH_3$ | $CF_3$ | H |
| 22 | 1-($CH_3$)-3-($CF_3CH_2O$)-pyrazol-5-yl | $CH_3$ | $CF_3$ | H |
| 23 | 3-($CF_3S$)-phenyl | $CH_3$ | CF | H |
| 24 | 3-($CF_3$)-phenyl | $CH_3$ | $C(CH_3)_3$ | H |
| 25 | 1-($C_2H_5$)-3-($CF_3$)-pyrazol-5-yl | $CH_3$ | $CF_3$ | H |
| 26 | 3-($CF_3$)-phenyl | $CH_3$ | $CH(CH_3)_2$ | H |
| 27 | 3-($CF_3$)-phenyl | $CH_3$ | Br | H |
| 28 | 1-($CH_3$)-3-($CF_3$)-4-F-pyrazol-5-yl | $CH_3$ | $CF_3$ | H |
| 29 | 1-($CH_3$)-3-($CF_3$)-4-Cl-pyrazol-5-yl | $CH_3$ | $CF_3$ | H |
| 30 | 1-($CH_3$)-3-($CF_3$)-pyrazol-5-yl | $CH_3$ | $CF_3O$ | H |
| 31 | 1-($CH_3$)-3-($CF_3$)-pyrazol-5-yl | $CH_3$ | $CF_3S$ | H |
| 32 | 1-($CH_3$)-3-($CF_3$)-pyrazol-5-yl | $CH_3$ | $CHF_2S$ | H |
| 33 | 1-($CH_3$)-3-($CF_3$)-pyrazol-5-yl | $CH_3$ | $C_2H_5$ | H |
| 34 | 1-($CH_3$)-3-($CF_3$)-pyrazol-5-yl | $CH_3$ | F | 3-F |
| 35 | 1-($CH_3$)-3-($CF_3$)-pyrazol-5-yl | $CH_3$ | F | 2-F |
| 36 | 1-($CH_3$)-3-($CF_3$)-pyrazol-5-yl | CN | $CF_3$ | H |
| 37 | 3-($CF_3$)-phenyl | CN | $CF_3$ | H |
| 38 | 3-($CF_3$)-phenyl | CN | Cl | H |
| 39 | 1-($CH_3$)-3-($CF_3$)-pyrazol-5-yl | CN | Cl | H |
| 40 | 2-Cl-pyrid-4-yl | CN | $CF_3$ | H |
| 41 | 2-($CF_3$)-pyrid-4-yl | CN | $CF_3$ | H |

EXAMPLES 42–46

Further Examples are prepared according to the general method of Example 1 and are listed in Table 2.

TABLE 2

[Structure: pyridine ring with F at 3,5 positions, R at 4-position, A-O at 6-position, and thiophene at 2-position bearing $R^3$]

| Ex. No. | A | R | $R^3$ |
|---|---|---|---|
| 42 | 3-($CF_3$)-phenyl | $CH_3$ | Cl |
| 43 | 1-($CH_3$)-3-($CF_3$)-pyrazol-5-yl | $CH_3$ | $CF_3$ |
| 44 | 3-($CF_3$)-phenyl | $CH_3$ | $CF_3$ |
| 45 | 1-($CH_3$)-3-($CF_3$)-pyrazol-5-yl | $CH_3$ | Cl |
| 46 | 1-($CH_3$)-3-($CF_3$)-pyrazol-5-yl | CN | Cl |

Herbicidal Activity

To evaluate their herbicidal activity, compounds according to the invention are tested using a representative range of plants:

| TRZAW | *Triticum aestivum* |
|---|---|
| HORVW | *Hordeum vulgare* |
| ZEAMX | *Zea mays* |
| ORYSA | *Oryza sativa* |
| GLXMA | *Glycine max* |
| ALOMY | *Alopecurus myosuroides* |
| SETVI | *Setaria viridis* |
| ABUTH | *Abutilon theophrasti* |
| AMARE | *Amaranthus retroflexus* |
| AMBEL | *Ambrosia artemisiifolia* |
| CHEAL | *Chenopodium album* |
| GALAP | *Galium aparine* |
| IPOHE | *Ipomoea hederacea* |
| MATIN | *Matricaria inodora* |
| STEME | *Stellaria media* |
| VERPE | *Veronica persica* |

The pre-emergence tests involve spraying a liquid formulation of the compound onto the soil in which the seeds of the plant species mentioned above has recently been sown.

The soil used in the tests is a prepared horticultural loam. The formulations used in the tests are prepared from solutions of the test compounds in acetone containing 0.4% by weight of an alkylphenol/ethylene oxide condensate available under the trade mark TRITON X-155. These acetone solutions are diluted with water and the resulting formulations applied at dosage levels corresponding to 12.5 g, 25 g, 100 g or 400 g of active material per hectare in a volume equivalent to 900 liters per hectare. In these tests untreated sown soil are used as controls.

From 2 to 4 weeks after treatment, the tests are terminated and each pot is examined and rated according to the rating system set forth below:

| Rating System | % Difference in Growth Versus Untreated Control |
|---|---|
| 0 - No effect | 0 |
| 1 - Trace effect | 1–5 |
| 2 - Slight effect | 6–15 |
| 3 - Moderate effect | 16–29 |
| 4 - Injury | 30–44 |
| 5 - Definite injury | 45–64 |
| 6 - Herbicidal effect | 65–79 |
| 7 - Good herbicidal effect | 80–90 |
| 8 - Approaching complete kill | 91–99 |
| 9 - Complete kill | 100 |

The results of the first assessment are set out in Table 3. An asterisk denotes that the specified plant species is not treated in the test.

TABLE 3

First assessment (pre-emergence application) 10 days after treatment

| Example | Dose kg/ha | GLXMA | HORVW | ORYSA | TRZAW | ZEAMX |
|---|---|---|---|---|---|---|
| No. 1 | 0.400 | 4 | 6 | 4 | 6 | X |
| No. 1 | 0.100 | 3 | 5 | 3 | 5 | 3 |
| No. 1 | 0.025 | 2 | 5 | 1 | 3 | 2 |
| No. 1 | 0.0125 | 2 | 4 | 1 | 3 | 1 |
| standard[1] | 0.400 | 5 | 6 | 6 | 6 | 5 |
| standard[1] | 0.100 | 5 | 6 | 5 | 5 | 5 |
| standard[1] | 0.025 | 3 | 5 | 3 | 5 | 4 |
| No. 2 | 0.400 | 6 | — | — | 4 | 3 |
| No. 2 | 0.100 | 3 | — | — | 1 | 2 |
| No. 2 | 0.025 | 1 | — | — | 1 | 1 |
| No. 2 | 0.0125 | 0 | — | — | 1 | 0 |
| standard[2] | 0.400 | 4 | 6 | 6 | 6 | 5 |
| standard[2] | 0.100 | 4 | 6 | 5 | 5 | 4 |
| standard[2] | 0.025 | 3 | 5 | 3 | 3 | 3 |

X = no value
— = not tested
[1]The following compounds, which are embraced by EP 0 723 960, have been used as standard:
standard[1]

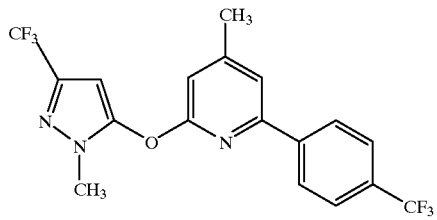

standard[2]

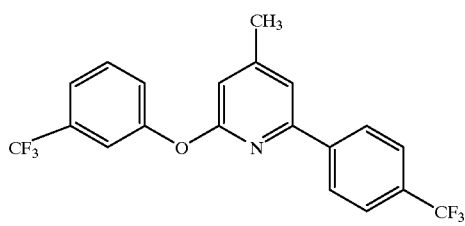

TABLE 4

Second assessment (pre-emergence application) 21 days after treatment

| Example | Dose kg/ha | GLXMA | HORVW | ORYSA | TRZAW | ZEAMX | ABUTH | AMBEL | GALAP | IPOHE | LAMPU | MATIN | STEME | VERPE | ALOMY | SETVI |
|---|---|---|---|---|---|---|---|---|---|---|---|---|---|---|---|---|
| No. 1 | 0.400 | 5 | 7 | 5 | 6 | X | 9 | — | 8 | 9 | X | 9 | 9 | 9 | 9 | 9 |
| No. 1 | 0.100 | 5 | 5 | 4 | 5 | 3 | 9 | — | 7 | 9 | X | 9 | 9 | 9 | 9 | 9 |
| No. 1 | 0.025 | 4 | 4 | 2 | 3 | 2 | 9 | — | 5 | 3 | X | 8 | 9 | 9 | 8 | 7 |
| No. 1 | 0.0125 | 4 | 4 | 2 | 3 | 1 | 6 | — | 3 | X | X | 8 | 9 | 8 | 7 | 7 |
| standard[1] | 0.400 | 7 | 6 | 6 | 6 | 5 | 9 | 9 | 9 | 9 | 9 | 9 | 9 | 9 | 9 | 9 |
| standard[1] | 0.100 | 6 | 5 | 5 | 5 | 5 | 9 | 9 | 7 | 9 | 9 | 9 | 9 | 9 | 9 | 9 |
| standard[1] | 0.025 | 4 | 5 | 4 | 5 | 4 | 9 | 9 | X | 8 | 9 | 9 | 9 | 9 | 8 | 9 |
| No. 2 | 0.400 | 7 | — | — | 5 | 3 | 8 | 9 | — | 7 | — | 9 | — | — | 9 | 9 |
| No. 2 | 0.100 | 4 | — | — | 1 | 2 | 3 | 5 | — | 3 | — | 8 | — | — | x | 9 |
| No. 2 | 0.025 | 2 | — | — | 0 | 1 | 1 | 5 | — | 2 | — | 8 | — | — | 3 | 8 |
| No. 2 | 0.0125 | 2 | — | — | 0 | 0 | 0 | 4 | — | 1 | — | 7 | — | — | 2 | 5 |
| standard[2] | 0.400 | 6 | 7 | 6 | 6 | 5 | 9 | 9 | 8 | 9 | 9 | 9 | 9 | 9 | 9 | 9 |
| standard[2] | 0.100 | 5 | 6 | 5 | 5 | 4 | 8 | 8 | 8 | 9 | 8 | 9 | 9 | 9 | 9 | 9 |
| standard[2] | 0.025 | 5 | 5 | 3 | 4 | 3 | 8 | 8 | 4 | 7 | 8 | 9 | 8 | 9 | 9 | 9 |

X = no value
— = not tested
[1]The same compounds have been used as standards as was used in the pre-emergence tests of Table 3.

The compounds of the invention have shown to clearly improve selectivity in important crops (maize, soybeans, wheat, barley) when compared to the corresponding compounds of the state of the art having a central 4-methylpyrid-2,6-diyl moiety instead of the 3,5-difluoro-4-methylpyrid-2,6-diyl group according to the invention. At the dose of 25 g/ha, which was well tolerated in rice, maize and wheat, the compound of example 1 demonstrated good overall levels of weed control while neither standard[1] nor standard[2] were sufficiently selective in these crops.

What is claimed is:

1. A compound of the formula (I):

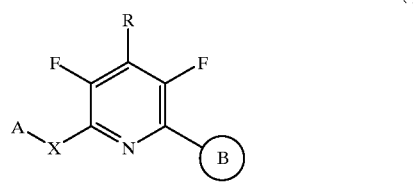

(I)

wherein
  A represents an optionally substituted aryl group or an optionally substituted 6-membered nitrogen-containing heteroaromatic group;
  B represents an optionally substituted phenyl or thienyl group;
  R represents a halogen atom or an optionally substituted alkyl, alkenyl, alkinyl, alkoxy, alkoxyalkyl, alkythio, alkylamino, dialkylamino, alkylsulphinyl, alkylsulphonyl group or a nitro, hydroxyl, amino, haloalkyl, haloalkoxy, haloalkylthio, or $SF_5$ group, and
  X represents an oxygen or a sulfur atom;
  and the agronomically acceptable salts or N-oxides thereof.

2. A compound as defined in claim 1, wherein A represents a phenyl or pyridyl group being substituted by one or more of the same of different substituents selected from halogen atoms, alkyl groups, alkoxy groups, cyano groups, haloalkyl groups, haloalkoxy groups, alkylthio groups, haloalkylthio groups and $SF_5$ groups.

3. A compound as defined in claim 1, wherein A has a substituent in the meta-position relative to the point of attachment.

4. A compound as defined in claim 3, wherein A is meta-substituted by a fluorine or chlorine atom, or a trifluoromethyl, trifluoromethoxy or difluoromethoxy group.

5. A compound as defined in claim 1, wherein B represents a phenyl or thienyl group being substituted by one or more of the same or different substituents selected from halogen atoms, alkyl groups, alkoxy groups, cyano groups, haloalkyl groups, haloalkoxy groups, alkylthio groups, haloalkylthio groups and $SF_5$ groups.

6. A compound as defined in claim 1, wherein X is oxygen.

7. A compound of formula IA:

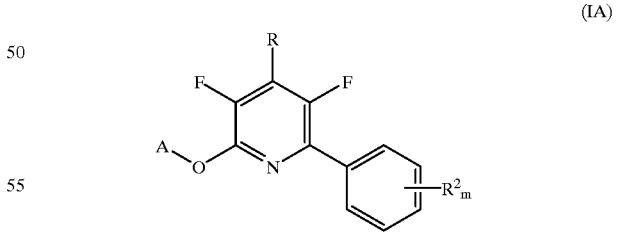

(IA)

wherein A represents 3-fluoromethylphenyl, 2-chloropyrid-4-yl, 2-trifluoromethylpyridyl-4yl, or 2-difluoromethoxypyrid-4-yl, R has the meaning given above; $R^2$ each independently represent a hydrogen atom or a fluorine atom, one or two of them also a chlorine or bromine atom or a trifluoromethyl, trifluoromethoxy or a cyano group, one of them can further be a $C_1$–$C_4$-alkyl group, particularly tert-butyl, and m is 0 or an integer selected from 1 to 5.

8. A compound selected from the group consisting of
3,5-difluoro-4-methyl-2-(3'-trifluoromethylphenoxy)-6-(4"-trifluoromethylphenyl)pyridine;
3,5-difluoro-4-ethyl-2-(3'-trifluoromethylphenoxy)-6-(4"-trifluoromethylphenyl)pyridine;
6-(4'-chlorophenyl)-3,5-difluoro-4-methyl-2-(3"-trifluoromethylphenoxy) pyridine;
2-(2'-chloropyrid-4'-yloxy)-3,5-difluoro-4-methyl-6-(4"-trifluoromethyl-phenyl)pyridine;
3,5-difluoro-4-methyl-2-(2'-trifluoromethylpyrid-4'-yloxy)-6-(4"-trifluoromethylphenyl)pyridine;
3,5-difluoro-2-(2'-difluoromethoxypyrid-4'-yloxy)-4-methyl-6-(4"-trifluoromethylphenyl)pyridine);
2-(2'-chloropyrid-4'-yloxy)-3,5-difluoro-4-methyl-6-(3"-trifluoromethylphenyl)pyridine;
3,5-difluoro-4-methoxy-2-(3'-trifluoromethylphenoxy)-6-(4"-trifluoromethylphenyl)pyridine;
3,5-difluoro-4-methyl-2-(2'-cyanopyrid-4'-yloxy)-6-(4"-trifluoromethylphenyl)pyridine;
3,5-difluoro-2-(3'difluoromethoxyphenoxy)-4-methyl-6-(4"-trifluoromethylphenlyl)pyridine;
3,5-difluoro-4-methyl-2-(3'-trifluoromethoxyphenoxy)-6-(4"-trifluoromethylphenyl)pyridine;
2-(3'-cyanophenoxy)-3,5-difluoro-4-methyl-6-(4"-trifluoromethylphenyl)pyridine;
3,5-difluoro-4-methyl-2-(2'-(2",2",2"-trifluoroethoxy)pyrid-4'-yloxy)-6-(4"-trifluoromethylphenyl)pyridine;
3,5difluoro-4-methyl-6-(4'-trifluoromethylphenyl)-2-(3"-trifluoromethylthylphenoxy)pyridine;
3,5-difluoro-4-methyl-6-(4'-tert-butyl-phenyl)-2-(3"-trifluoromethylphenoxy)-pyridine;
3,5-difluoro-4-methyl-6-(4'-isopropylphenyl)-2-(3"-trifluoromethylphenoxy)-pyridine;
6-(4'-bromophenyl)-3,5-difluoro-4-methyl-2-(3"-trifluoromethylphenoxy)pyridine;
3,5-difluoro-4-chloro-2-(3'-trifluoromethylphenloxy)-6-(4"-trifluoromethylphenyl)pyridine;
3,5difluoro-4-methylthio-2-(3'-trifluoromethylphenoxy)6(4"-trifluoromethylphenyl )pyridine.

9. A process for the preparation of a compound of formula I, which comprises reacting a respective compound of the general formula II:

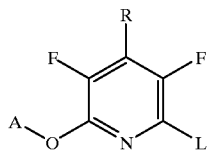

(II)

in which A and R have the meaning given in claim 1 and L is a leaving group, with a compound of general formula III:

(III)

in which B has the meaning given in claim 1, and M represents a free or complexed metal selected from the group consisting of Li, Mg, B, and Sn.

10. A process for the preparation of a compound of formula I, as claimed in claim 1 which comprises reacting a respective compound of the general formula IV:

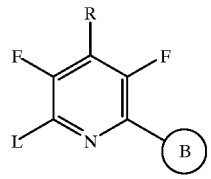

(IV)

with a compound of general formula V:

A—XM¹  (V)

wherein

A, B, R and X are defined as in claim 1;

L represents a suitable leaving group; and $M^1$ represents a metal atom.

11. A herbicidal composition comprising at least one compound of general formula I, as claimed in claim 1, together with a carrier.

12. A composition as defined in claim 11, comprising at least two carriers, at least one of which is a surface-active agent.

13. A method of combating undesired plant growth at a locus, comprising application to the locus of a compound of formula I, as claimed in claim 1 or of a composition comprising at least one compound of formula I, as defined in claim 1, together with a carrier, or comprising at least two carriers, at least one of which is a surface-active agent.

* * * * *

UNITED STATES PATENT AND TRADEMARK OFFICE
CERTIFICATE OF CORRECTION

PATENT NO. : 6,673,745 B2
DATED : January 6, 2004
INVENTOR(S) : Maier et al.

It is certified that error appears in the above-identified patent and that said Letters Patent is hereby corrected as shown below:

Column 20,
Line 60, "4-yI" should be -- 4-yl --.

Column 21,
Line 29, "trifluoromethylthylphenoxy" should be -- trifluoromethylthiophenoxy --.
Line 41, after "I" insert -- as claimed in claim 1 --.

Signed and Sealed this

Eighth Day of June, 2004

JON W. DUDAS
*Acting Director of the United States Patent and Trademark Office*